United States Patent [19]
Umber et al.

[11] Patent Number: 5,827,288
[45] Date of Patent: Oct. 27, 1998

[54] CIRCULAR HOLE FORMING APPARATUS

[75] Inventors: Ray Umber; Townsend R. Scantlebury, both of Arlington, Tex.

[73] Assignee: Midas Rex, L.P., Fort Worth, Tex.

[21] Appl. No.: 833,928

[22] Filed: Apr. 10, 1997

[51] Int. Cl.$^6$ .................................................. A61B 17/56
[52] U.S. Cl. ............................... 606/80; 606/96; 606/180
[58] Field of Search ................................. 606/96, 86, 87, 606/88, 89, 80, 79, 85

[56] References Cited

U.S. PATENT DOCUMENTS

| | | | |
|---|---|---|---|
| 3,308,828 | 3/1967 | Pippin . | |
| 4,596,243 | 6/1986 | Bray . | |
| 4,860,735 | 8/1989 | Davey et al. | 606/96 |
| 4,952,214 | 8/1990 | Comparetto . | |
| 5,207,681 | 5/1993 | Ghadjar et al. | 606/96 |
| 5,534,005 | 7/1996 | Tokish, Jr. et al. | 606/80 |
| 5,613,970 | 3/1997 | Houston et al. | 606/88 |
| 5,616,146 | 4/1997 | Murray | 606/80 |

Primary Examiner—Guy V. Tucker
Attorney, Agent, or Firm—James E. Bradley

[57] ABSTRACT

A surgical guide tool has an axis and a cylindrical housing with a central bore, an upper cylindrical wall and a flange that are aligned with the axis. The tool has adjustable legs with a sharp conical point and a guide disk with a cylindrical body that lands within the wall. The guide disk has an eccentric bore that extends through the guide disk. A cylindrical cap encloses the guide disk within the tool. The upper end of the guide disk protrudes through a central hole in the cap and a lever is secured to the upper end of the guide disk. The guide disk is free to rotate within the tool. After a starter hole is made in a human skull, the tool is placed over the starter hole with the legs landing on the skull. A conventional surgical cutting implement with a footed attachment is inserted into the guide disk bore. The footed attachment is placed in the starter hole beneath the skull. The surgeon applies a tangential force to the lever to rotate the guide disk and implement within the tool around the axis so that a cranial flap is made.

12 Claims, 2 Drawing Sheets

CIRCULAR HOLE FORMING APPARATUS

TECHNICAL FIELD

This invention relates in general to medical devices, and in particular to surgical guide tools.

BACKGROUND ART

In surgical procedures requiring an opening in the skull, it is often difficult to create a precise opening in a specific location on the skull. There is also considerable danger of penetration of the dura, a membrane lying between the brain and the skull. One prior art patent discloses an oscillating core drill which is difficult to maintain in one location.

Another prior art patent discloses a bone saw guide for making arcuate saw cuts. This device guides a bone saw through a circular path from a single pivot point in a compass-like fashion, but is difficult to precisely control along the path and in depth of cut.

Yet another prior art technique involves the use of a fluted drill to drill a series of burr holes in the cranium around the section of cranium to be removed. A cutting tool is then inserted to join the holes. This procedure requires a significant amount of time and results in considerable loss of bone. None of these prior art devices provides an instrument which gives a surgeon very precise control of the cutting implement with minimal slippage or misalignment of the tool.

DISCLOSURE OF INVENTION

A surgical guide tool has an axis and a cylindrical housing. The housing has a central bore, an upper cylindrical wall and a flange that are aligned with the axis. The radially outer surface of the wall is threaded. The flange has a plurality of threaded holes located near its outer edge that are symmetrically arranged around the axis.

The tool has a plurality of legs equal to the number of threaded holes. The legs have threads for mating engagement with the threaded holes, and a sharp conical point. The tool also has a guide disk with a cylindrical body. The lower surface of the body lands within the wall on the upper surface of the housing. The guide disk has a lower hub which seats in the bore of the housing. A second bore, which is eccentric to the axis, extends through the guide disk.

A cylindrical cap having a base and a lower wall at its outer edge encloses the guide disk within the tool. The inner surface of the cap wall threadingly engages the outer surface of the housing wall. The upper hub on the guide disk protrudes upward through and is closely received by a central hole in the cap. A lever is secured to the upper surface of the upper hub. The lever has a notch which provides a clearance for access to the guide disk bore.

The tool is used to assist a surgeon in making a precise opening in the skull of a patient. To assemble the tool, the legs are threaded into the housing. The guide disk is placed in the housing so that its lower hub seats in the bore. The cap is threaded onto the housing to retain the guide disk in the tool and the lever is secured to the upper hub. The guide disk is free to rotate within the tool.

A small starter hole is made in the skull with a conventional surgical cutting tool. The tool is placed over the starter hole with the legs landing on the skull. The legs are adjusted to the proper height so that each point slightly embeds in the skull to prevent further movement of the tool. A conventional surgical cutting implement with a footed attachment is inserted into the guide disk bore. The footed attachment is placed in the starter hole beneath the skull. With the tool secured from movement, the surgeon applies a tangential force to the lever to rotate the guide disk and implement within the tool around the axis. The surgeon carefully guides the implement so that a cranial flap is made. The implement and the tool are then removed from the patient.

BEST MODE FOR CARRYING OUT THE INVENTION

Figure 1:
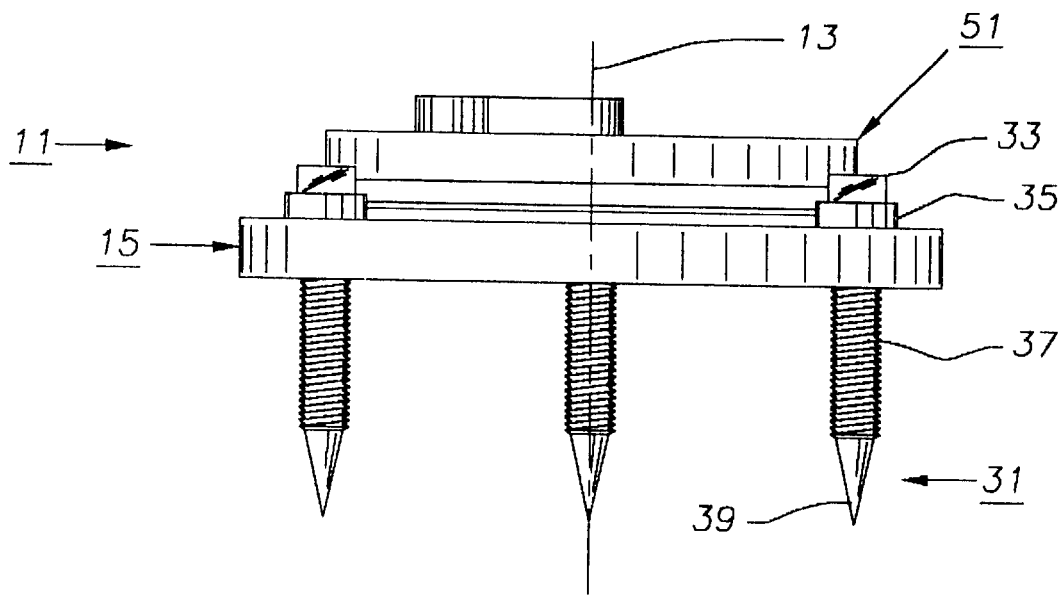
FIG. 1 is a side view of a surgical instrument constructed in accordance with the invention.
Figure 2:
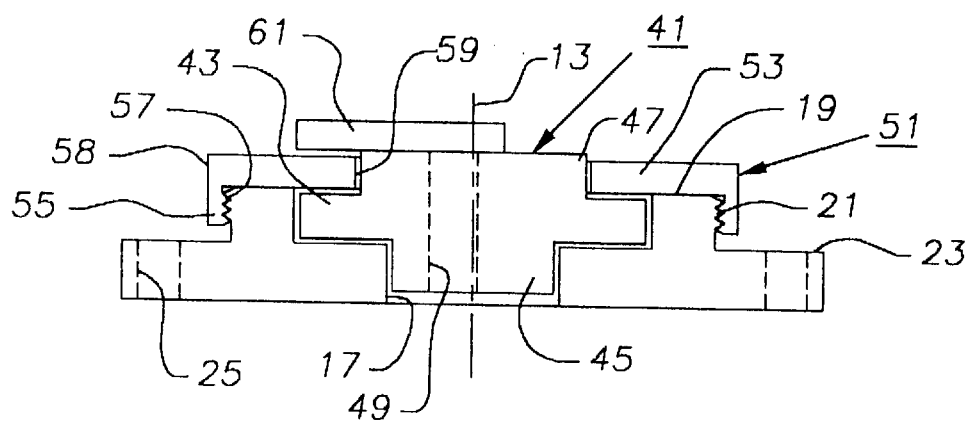
FIG. 2 is a sectional side view of the surgical instrument of FIG. 1.

Referring to FIGS. 1 and 2, a surgical guide tool 11 with an axis 13 is shown. Tool 11 has a circular housing or back plate 15 which has a central bore 17, an upper cylindrical wall 19 and a flange 23 that are aligned with axis 13. Wall 19 is located between bore 17 and the outer edge of flange 23. Wall 19 extends above flange 23 for a height that is approximately equal to the height of flange 23. The radially outer surface 21 of wall 19 is threaded. Flange 23 extends radially outward from wall 19. Flange 23 has a plurality of threaded holes 25 located near its outer edge that are symmetrically arranged around axis 13.

Tool 11 has a plurality of legs 31 equal to the number of holes 25. In the preferred embodiment, tool 11 has three legs 31 and three holes 25. Legs 31 have a square head 33, a shoulder 35, threads 37 for mating engagement with threaded holes 25, a sharp conical point 39, and a length which is approximately half the diameter of back plate 15. Legs 31 may be adjustably threaded into holes 25 until shoulder 35 bottoms-out on the upper surface of flange 23. Point 39 is designed to embed slightly in a skull.

Tool 11 has a guide disk 41 which has a cylindrical body 43. Body 43 has an outer diameter which is slightly less than the inner diameter of wall 19 and a height that is slightly less than the height of wall 19. The lower surface of body 43 lands within wall 19 on the upper surface of back plate 15. Guide disk 41 has a lower hub 45 which seats in bore 17. The diameter of lower hub 45 is approximately equal to the diameter of bore 17. Guide disk 41 also has an upper hub 47 which has a diameter which is greater than the diameter of lower hub 45. Body 43 is slightly thicker than lower hub 45, while lower hub 45 is thicker than upper hub 47. A bore 49, which is eccentric to axis 13, extends through guide disk 41 from upper hub 47 to lower hub 45.

A cylindrical cap 51 having a base 53 and a lower wall 55 at its outer edge encloses guide disk 41 within tool 11. Base 53 has a height which is less than the height of upper hub 47. Wall 55 has an outer diameter which is greater than the outer diameter of wall 19, but less than the outer diameter of flange 23. The inner surface 57 of wall 55 threadingly engages threads 21 on wall 19. The outer surface 58 of wall 55 is knurled to provide a better grip. Upper hub 47 protrudes upward through a central hole 59 in cap 51 which closely receives upper hub 47.

Figure 4:
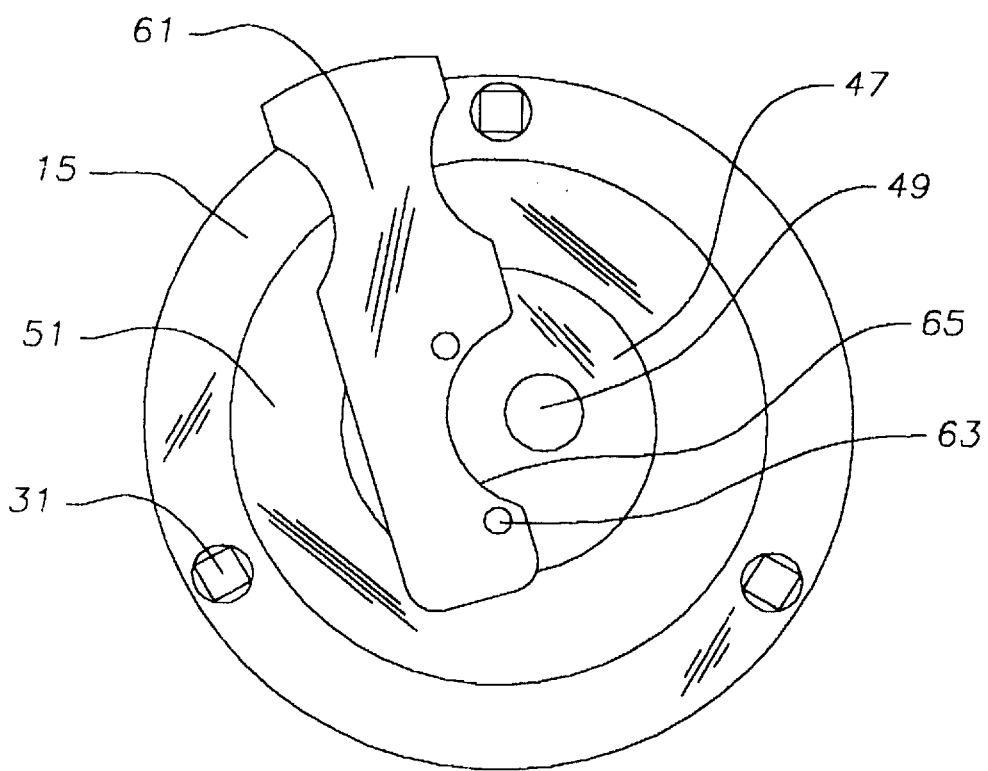
FIG. 4 is a top view of the surgical instrument of FIG. 1.

As shown in FIG. 4, an ergonomically shaped handle or lever 61 is rigidly secured to the upper surface of upper hub 47 with pins 63 which extend through lever 61 and into guide disk 41. Lever 61 has a length which is approximately equal to the diameter of cap 51, and a thickness which is approximately equal to the height of flange 23. Lever 61 has a notch 65 which provides a clearance for access to bore 49 in guide disk 41.

In operation, tool 11 will be used to assist a surgeon in making a precise opening in the skull of a patient (not shown). To assemble tool 11, legs 31 are threaded into holes 25 in back plate 15. Guide disk 41 is placed in back plate 15 so that lower hub 45 seats in bore 17. Cap 51 is threaded onto back plate 15 to retain guide disk 41 in tool 11. Lever 61 is secured to upper hub 47 which protrudes upward through cap 51. Guide disk 41 is free to rotate within tool 11. Lever 61 rotates with guide disk 41.

Figure 3:
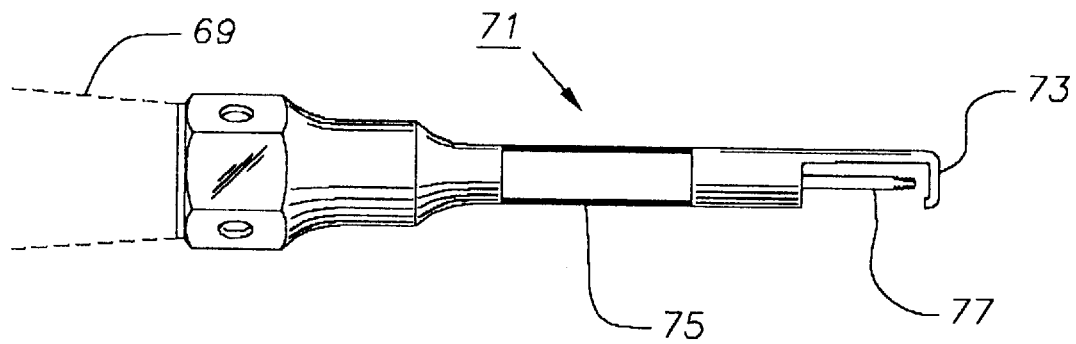
FIG. 3 is a side view of a footed surgical drilling tool.

A small starter hole is made in the skull at the site of incision with a conventional surgical cutting tool (not shown). Tool 11 is placed over the starter hole with legs 31 landing on the skull such that bore 49 is vertically aligned with the starter hole. Legs 31 are threadingly adjusted to the proper height so that each point 39 slightly embeds in the skull to prevent further movement of tool 11. Referring to FIG. 3, a conventional surgical cutting implement 71 is inserted into bore 49 and is closely received by tool 11. Implement 71 is powered by a pneumatic motor 69. A cutting bit 77 and a footed attachment 73 extend from one end of implement 71. Bit 77 rotates at high speed within implement 71 to cut bone. Bit 77 does not make contact with attachment 73. Implement 71 has a shaft midsection 75 which seats within bore 49, but is substantially free to rotate within bore 49. Footed attachment 73 is placed in the starter hole beneath the skull and prevents bit 77 from damaging the underlying dura.

With tool 11 secured from lateral movement, the surgeon applies a tangential force to lever 61. This force rotates guide disk 41 within tool 11 around axis 13 and rotates implement 71 through a precise circular path. Implement 71 makes an orbital path around axis 13. The surgeon carefully guides lever 61 and implement 71 completely through the circular path so that a cranial flap is made. Implement 71 and tool 11 are then removed from the patient.

The invention has several advantages. After defining the location for cranial incision and creating a starter hole, a surgeon can create a precise circular opening in a skull while reducing the danger of penetration of the dura. The invention is easily maintained in its precise location with sharp legs. The invention also makes the path and depth of cut of the cutting implement easier to control. Finally, the procedure suggested by the invention requires relatively less time and loss of bone.

While the invention has been shown in only one of its forms, it should be apparent to those skilled in the art that it is not so limited, but is susceptible to various changes without departing from the scope of the invention.

We claim:

1. A medical device for facilitating the creation of an opening in a skull, comprising in combination:
   a housing having a cylindrical wall;
   a plurality of locators for precisely locating the housing in engagement with the skull;
   a guide member mounted to the housing for rotation relative to the housing about an axis, the guide member having a cylindrical wall which slidingly engages the cylindrical wall of the housing; and
   a hole extending through the guide member for receiving a surgical bone cutting implement, the hole being offset from the axis so that rotating the guide member causes the implement to move through a circular path.

2. The medical device of claim 1 wherein the plurality of locators comprises a plurality of legs mounted to the housing for adjustment along the housing, the legs having a sharp point on one end.

3. The medical device of claim 1 further comprising threaded holes in the housing; and wherein
   the plurality of locators comprises a plurality of threaded legs located in the threaded holes for adjustment along the housing, the legs having a sharp point on one end and extending in a substantially perpendicular direction relative to the housing.

4. The medical device of claim 1 wherein the guide member comprises a cylindrical guide disk.

5. The medical device of claim 1 further comprising a handle secured to the guide member for rotating the guide member.

6. A medical device for facilitating the creation of an opening in a skull, comprising in combination:
   a pneumatic bone cutting implement;
   a housing having a central bore and a cylindrical inner wall;
   a plurality of legs mounted to the housing for adjustment along the housing, the legs extending in a substantially perpendicular direction relative to the housing and having a sharp point on one end for precisely locating the housing in engagement with the skull;
   a generally cylindrical guide member having a cylindrical outer wall for slidingly engaging the cylindrical inner wall of the housing, the guide member being mounted to the housing for rotation relative to the housing about an axis;
   the guide member having a bore which is eccentric to the axis, the bore receiving the pneumatic bone cutting implement so that rotation of the guide member causes the implement to move through a circular path; and
   a handle secured to the guide member, the handle facilitating the rotation of the guide member and the implement.

7. The medical device of claim 6, further comprising a cap secured to the housing over the guide member and having a central hole which exposes the bore of the guide member for accommodating the implement.

8. The medical device of claim 6 wherein the hub has an upper portion located on an upper side of the guide member; and wherein the medical device further comprises:
   a cap secured to the housing over the guide member and having a central hole which exposes the bore of the guide member for accommodating the upper portion of the hub and the implement.

9. The medical device of claim 6 wherein the implement further comprises a footed attachment.

10. A medical device for facilitating the creation of an opening in a skull, comprising in combination:
    a pneumatic bone cutting implement;
    a housing having a central bore;
    a plurality of legs mounted to the housing for adjustment along the housing, the legs having a sharp point on one end for precisely locating the housing in engagement with the skull;
    a guide member having a hub, the guide member being mounted to the housing for rotation relative to the housing about an axis, the hub having an upper portion on an upper side of the guide member and a lower portion which seats in the bore of the housing;
    the guide member having a bore which is eccentric to the axis, the bore receiving the pneumatic bone cutting implement so that rotation of the guide member causes the implement to move through a circular path;

a handle secured to the guide member, the handle facilitating the rotation of the guide member and the implement;

a cap secured to the housing over the guide member and having a central hole which exposes the bore of the guide member for accommodating the upper portion of the hub and the implement; and wherein the bore of the guide member extends through the hub and the guide member.

11. A medical device for facilitating the creation of an opening in a skull, comprising in combination:

a pneumatic bone cutting implement;

a housing having a central bore;

a plurality of legs mounted to the housing for adjustment along the housing, the legs having a sharp point on one end for precisely locating the housing in engagement with the skull;

a guide member having a hub, the guide member being mounted to the housing for rotation relative to the housing about an axis, the hub having an upper portion on an upper side of the guide member and a lower portion which seats in the bore of the housing;

the guide member having a bore which is eccentric to the axis, the bore receiving the pneumatic bone cutting implement so that rotation of the guide member causes the implement to move through a circular path; and a handle secured to the guide member, the handle facilitating the rotation of the guide member and the implement;

a cylindrical wall located on an upper side of the housing, the wall on the housing having threads on a radially outer surface;

a cap having inner threads which engage the threads on the wall of the housing to rotatingly secure the guide member therebetween, the cap also having a central hole which exposes the bore of the guide member for accommodating the hub and the implement; and wherein the bore of the guide member extends through the hub and the guide member.

12. A method of creating an opening in a skull, comprising:

providing a guide tool, a housing, a plurality of adjustable legs and a guide disk which is rotatable about an axis and has an eccentric bore;

locating and forming a starter hole in the skull with a surgical tool;

landing the guide tool over the starter hole in the skull and adjusting the legs such that the bore is centered directly over the starter hole and the legs engage the skull to limit the movement of the guide tool;

inserting a surgical bone cutting implement through the bore, the implement having a footed attachment and a cutting tip;

inserting the footed attachment into the starter hole beneath the skull;

rotating the cutting tip of the implement and the guide disk about the axis, causing the cutting tip to cut a circular path in the skull around the axis.

* * * * *